(12) United States Patent
Gregerson et al.

(10) Patent No.: US 8,753,009 B2
(45) Date of Patent: Jun. 17, 2014

(54) DRIVE SYSTEM FOR IMAGING DEVICE

(75) Inventors: Eugene A. Gregerson, Bolton, MA (US); Russell Stanton, Lunenberg, MA (US); Michael Allen, Boxborough, MA (US); Michael Connor, Tyngsboro, MA (US); Scott Coppen, Amesbury, MA (US)

(73) Assignee: Mobius Imaging, LLC, Ayer, MA (US)

( * ) Notice: Subject to any disclaimer, the term of this patent is extended or adjusted under 35 U.S.C. 154(b) by 562 days.

(21) Appl. No.: 13/025,566

(22) Filed: Feb. 11, 2011

(65) Prior Publication Data

US 2011/0222667 A1 Sep. 15, 2011

Related U.S. Application Data

(60) Provisional application No. 61/313,299, filed on Mar. 12, 2010.

(51) Int. Cl.
| | |
|---|---|
| *H05G 1/02* | (2006.01) |
| *A61B 6/03* | (2006.01) |
| *A61B 6/00* | (2006.01) |

(52) U.S. Cl.
CPC .............. *A61B 6/035* (2013.01); *A61B 6/4405* (2013.01); *A61B 6/4429* (2013.01); *G01N 2223/301* (2013.01); *G01N 2223/308* (2013.01); *G01N 2223/3303* (2013.01)
USPC .............................. 378/196; 378/197; 378/198

(58) Field of Classification Search
CPC ........ A61B 6/035; A61B 6/44; A61B 6/4405; A61B 6/4411; A61B 6/4429; G01N 2223/30; G01N 2223/301; G01N 2223/308; G01N 2223/32; G01N 2223/321; G01N 2223/33; G01N 2223/3303
USPC ............................................... 378/4, 195–198
See application file for complete search history.

(56) References Cited

U.S. PATENT DOCUMENTS

| | | | |
|---|---|---|---|
| 4,928,283 A | * | 5/1990 | Gordon ........................... 378/20 |
| 4,935,949 A | | 6/1990 | Fujita et al. |
| 4,977,588 A | | 12/1990 | Van der Ende |
| 5,081,662 A | | 1/1992 | Warden et al. |
| 5,448,607 A | | 9/1995 | McKenna |

(Continued)

OTHER PUBLICATIONS

International Search Report and Written Opinion issued in PCT Application No. PCT/US2011/024585, mailed on Apr. 4, 2011.

(Continued)

*Primary Examiner* — Thomas R Artman
(74) *Attorney, Agent, or Firm* — The Marbury Law Group, PLLC

(57) ABSTRACT

A drive mechanism for a mobile imaging system comprises a main drive geared into a drive wheel for propelling the imaging system, including a base and one or more imaging components, across a surface. The drive mechanism can also include a scan drive that moves the drive mechanism and the one or more imaging components along an axis relative to the base to provide an imaging scan, and a suspension drive that extends the drive wheel relative to a bottom surface when the imaging system is in a transport mode and retracts the drive wheel relative to the bottom surface of the base when the imaging system is in an imaging mode. The drive wheel supports the weight of the imaging components, but does not directly support the base assembly, which can include pedestal and tabletop support. One or more casters located on the base can support the weight of the base assembly.

43 Claims, 15 Drawing Sheets

(56) References Cited

U.S. PATENT DOCUMENTS

| | | | |
|---|---|---|---|
| 5,638,419 A | 6/1997 | Ingwersen | |
| 6,131,690 A * | 10/2000 | Galando et al. | 180/411 |
| 6,212,251 B1 * | 4/2001 | Tomura et al. | 378/15 |
| 6,456,684 B1 * | 9/2002 | Mun et al. | 378/20 |
| 6,959,068 B1 * | 10/2005 | Sommer | 378/20 |
| 7,001,045 B2 | 2/2006 | Gregerson et al. | |
| 7,175,347 B2 * | 2/2007 | Tybinkowski et al. | 378/198 |
| 7,388,941 B2 | 6/2008 | Sukovic et al. | |
| 7,397,895 B2 | 7/2008 | Bailey et al. | |
| 7,438,471 B2 | 10/2008 | Tybinkowski et al. | |
| 7,490,982 B2 | 2/2009 | Gregerson et al. | |
| 2005/0135560 A1 | 6/2005 | Dafni et al. | |
| 2007/0092068 A1 * | 4/2007 | Albert | 378/198 |
| 2008/0123818 A1 * | 5/2008 | Alder et al. | 378/198 |
| 2009/0236157 A1 | 9/2009 | Akamatsu | |
| 2010/0172468 A1 | 7/2010 | Gregerson | |
| 2012/0104264 A1 | 5/2012 | Bailey et al. | |

OTHER PUBLICATIONS

International Preliminary Report on Patentability issued in PCT Application No. PCT/US2011/024585, mailed on Sep. 27, 2012.

* cited by examiner

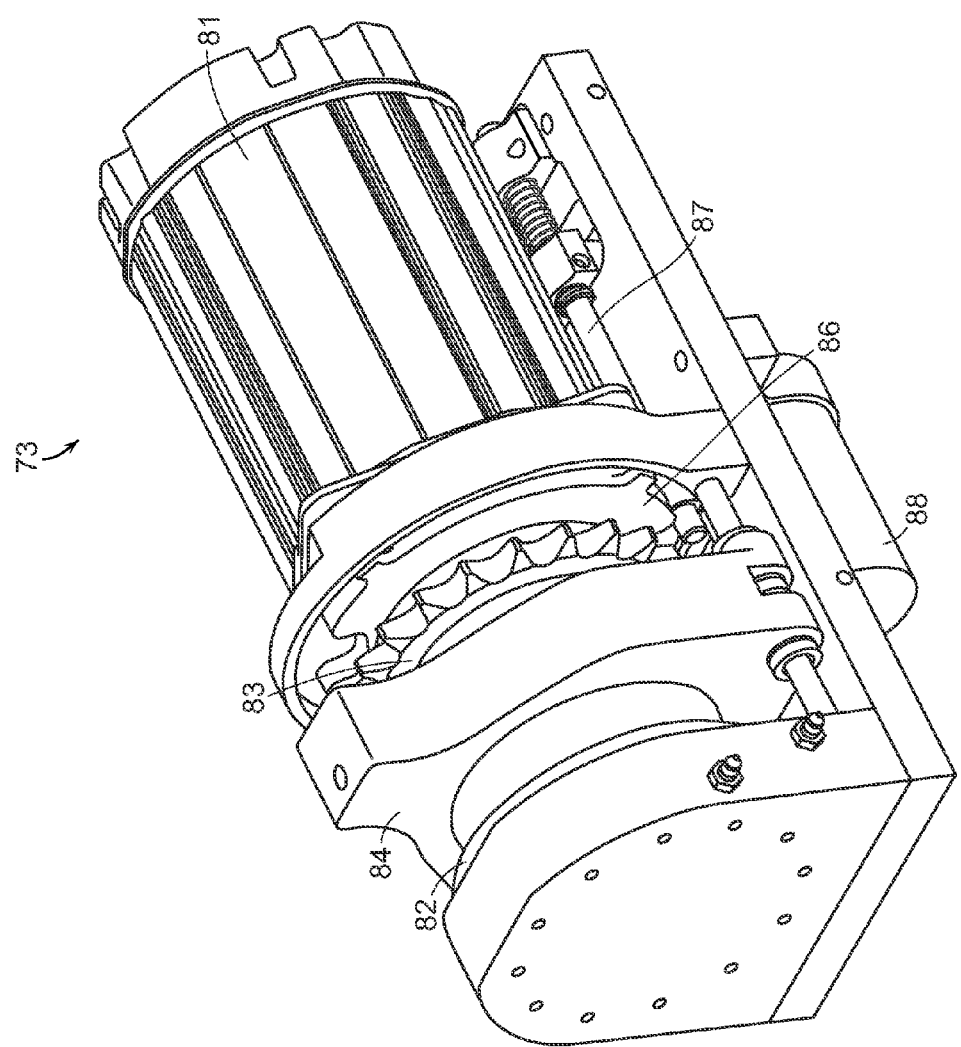
FIG. 11B

DRIVE SYSTEM FOR IMAGING DEVICE

CROSS-REFERENCE TO RELATED APPLICATION

This application claims the benefit of U.S. Provisional Application No. 61/313,299, filed Mar. 12, 2010, the entire contents of which are incorporated herein by reference.

STATEMENT REGARDING FEDERALLY SPONSORED RESEARCH OR DEVELOPMENT

N/A

BACKGROUND OF THE INVENTION

Conventional medical imaging devices, such as computed tomography (CT) and magnetic resonance (MR) imaging devices, are typically fixed, immobile devices located in a discrete area reserved for imaging that is often far removed from the point-of-care where the devices could be most useful.

It would be desirable to make these imaging devices mobile, so that they can move to various locations within a hospital or other health services environment. This is difficult due to the size, weight and overall number of components required for making an operable imaging system, and even a relatively small and compact imaging device, such as an x-ray CT scanner, can weigh upwards of 2500 lbs.

There is a need to improve the mobility of imaging systems without sacrificing image quality or adding significantly to the size and weight of the device.

SUMMARY OF THE INVENTION

A drive mechanism for a mobile imaging system comprises a drive wheel, and a main drive geared into a drive wheel for propelling the imaging system across a surface in a transport mode. The imaging system includes a base and one or more imaging components. The drive mechanism further translates one or more imaging components along an axis relative to the base in an imaging mode, where the one or more imaging components are supported by the drive wheel in both the transport mode and the imaging mode.

The drive mechanism can further comprise a scan drive that translates the one or more imaging components along an axis relative to the base to provide an imaging scan, and a suspension drive that extends the drive wheel relative to a bottom surface of the base when the imaging system is in a transport mode. The suspension drive retracts the drive wheel relative to the bottom surface of the base when the imaging system is in an imaging mode.

According to one aspect, the drive wheel supports the weight of the imaging components, but does not directly support the base assembly, which can include a pedestal and tabletop support. One or more casters located on the base can support the weight of the base assembly.

The drive mechanism can be positioned within the base, preventing interference with a patient table shuttle when driving up to the base and also preventing interference with an operator's feet while standing at the table.

During scanning, the drive wheel supports the weight of the imaging components, which can be located on a gantry positioned above the drive mechanism. The base is positioned on the floor, on at least three support pads attached to the bottom of the base that define a scanning plane, which minimizes or eliminates deflection of the base during scanning due to an uneven floor surface.

In an imaging mode, the drive wheel and casters retract to allow the base to sit on the support pads to create a scan plan. In a transport mode, the drive wheel and casters extend for transporting the imaging system.

In one embodiment, the drive wheel is servo controlled and tied to a user drive system on the imaging system, which allows the system to feel weightless during transport.

In one embodiment, the drive wheel has an active servo-controlled suspension to allow for smooth movement over thresholds, bumps in the floor and ramps when transporting the system.

In certain embodiments, a mobile imaging system includes a drive mechanism as described above. Additional embodiments relate to methods of imaging using a drive mechanism of the invention.

In preferred embodiments, the drive mechanism is extremely compact, which allows the entire drive system to be hidden from view, such as beneath the gantry and gimbal assembly and inside the base, while not interfering with operation of the imaging system.

BRIEF DESCRIPTION OF THE SEVERAL VIEWS OF THE DRAWINGS

Other features and advantages of the present invention will be apparent from the following detailed description of the invention, taken in conjunction with the accompanying drawings of which:

FIGS. 11A and 11B are top isometric views of the main drive assembly;

DETAILED DESCRIPTION OF THE INVENTION

This application claims the benefit of U.S. Provisional Application No. 61/313,299, filed Mar. 12, 2010, and is related to U.S. application Ser. No. 12/576,681, filed Oct. 9, 2009, and to U.S. Provisional Application No. 61/315,462, filed Mar. 19, 2010. The entire contents of the above-referenced applications are incorporated herein by reference.

Figure 2:
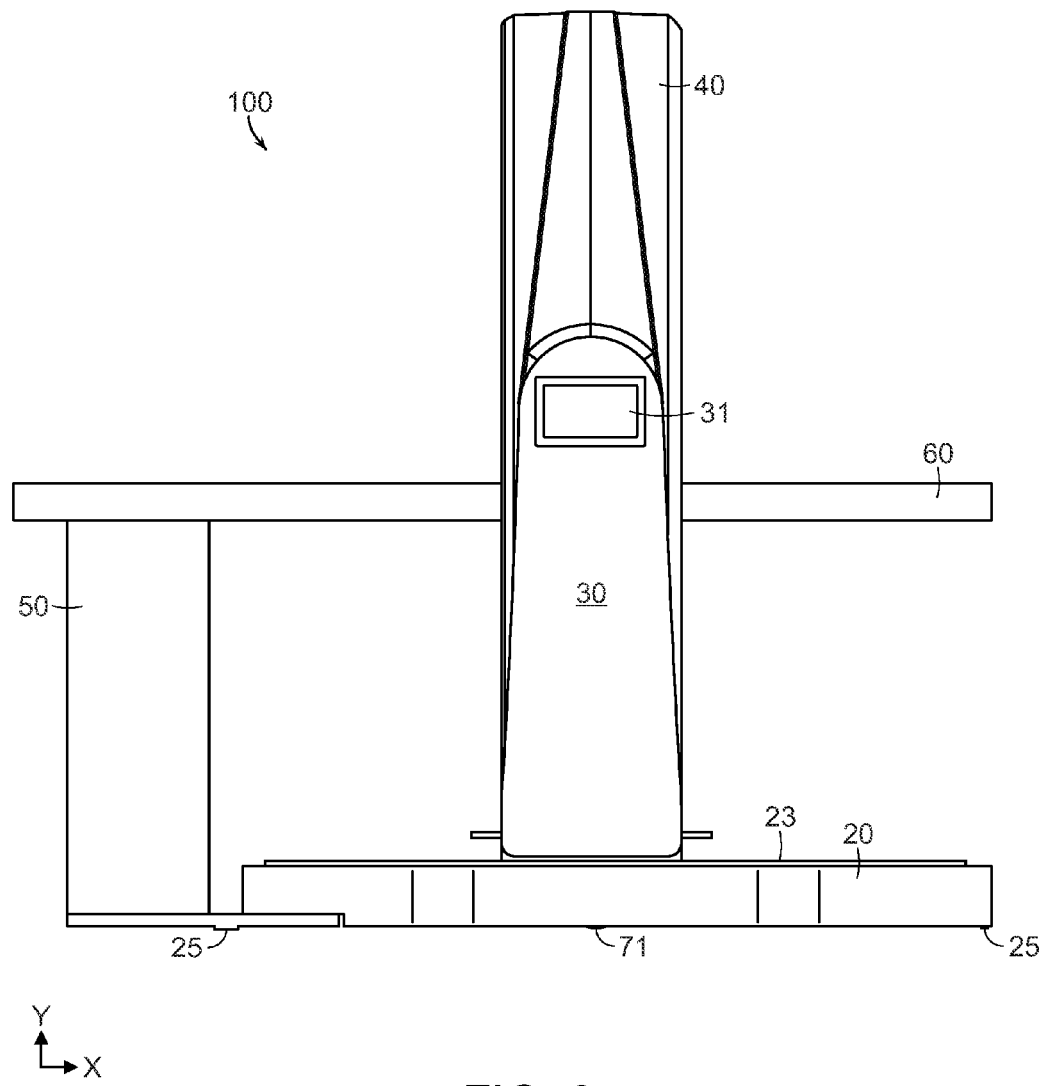
FIG. 2 is a side view of the mobile imaging system with the drive wheel and casters retracted and the base lowered to the floor.
Figure 3:
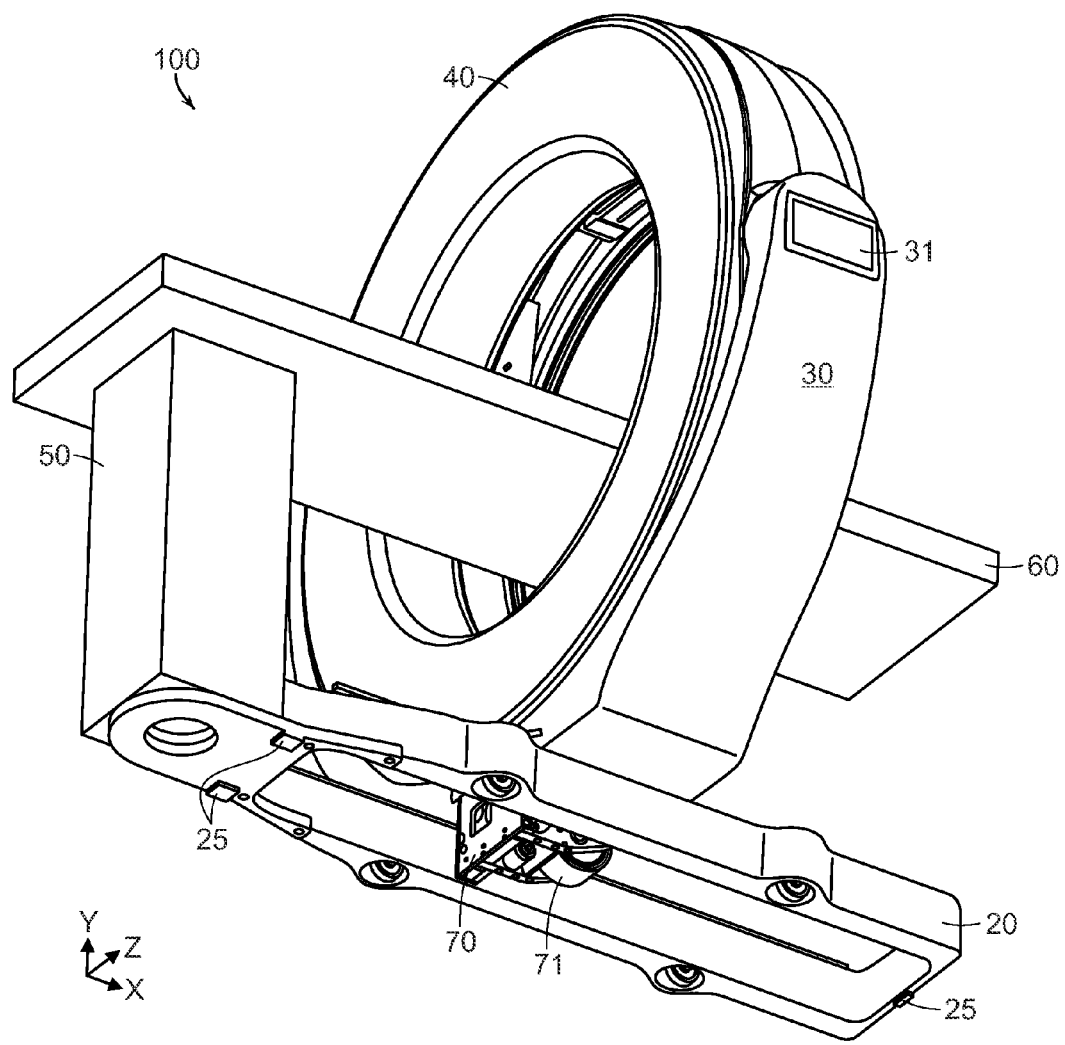
FIG. 3 is a bottom isometric view of the imaging system showing the drive wheel and casters retracted and pads on the bottom surface of the base that define a scan plane.
Figure 4:
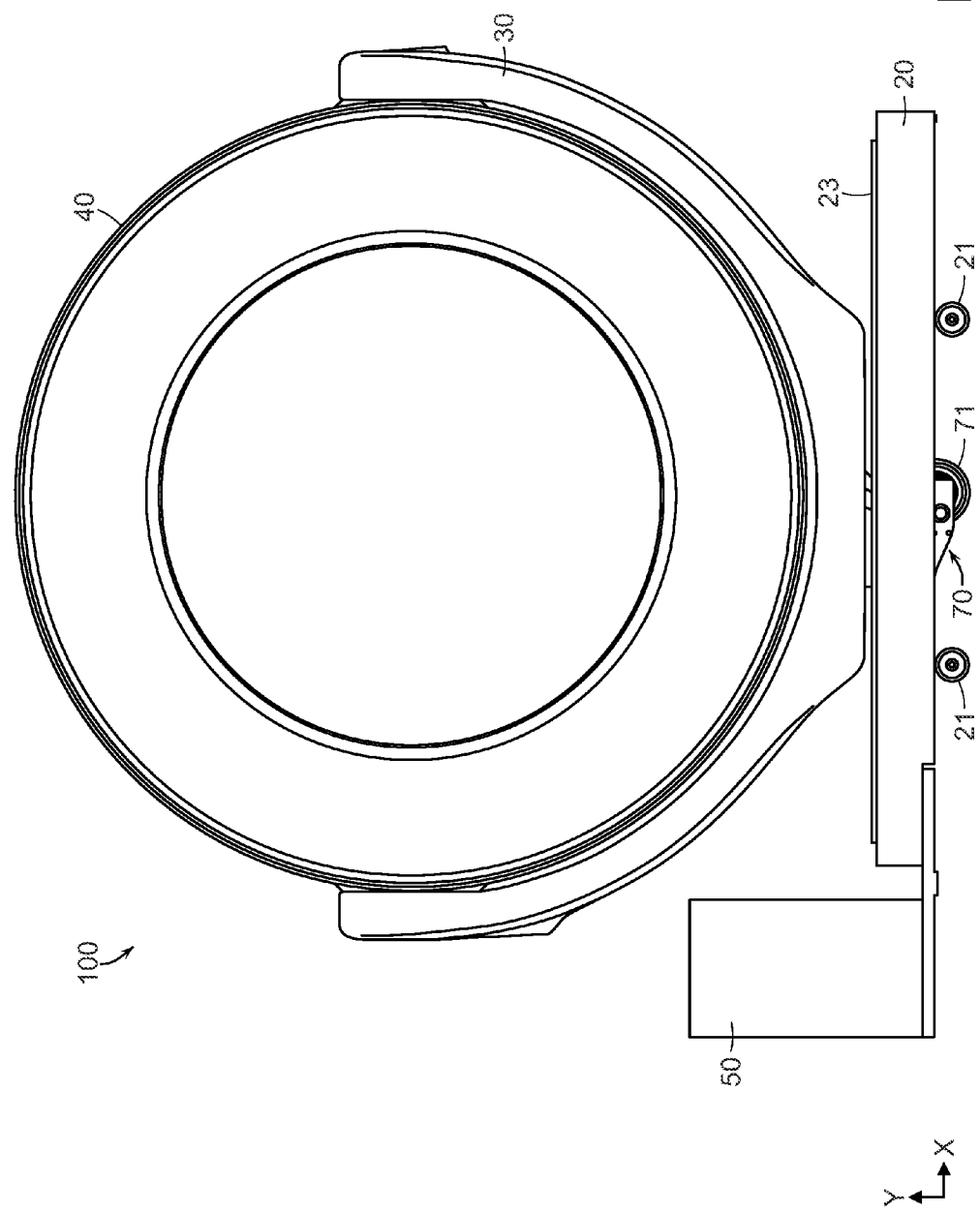
FIG. 4 is a side view of the mobile imaging system in a transport mode.

Referring to FIGS. 1-5, a mobile imaging system 100 according to one embodiment of the invention includes a mobile base 20, a gimbal support 30, a gantry ring 40, and a pedestal 50. The system 100 includes image collection components, such as a rotatable x-ray source and detector array or stationary magnetic resonance imaging components, that are housed within the gantry ring 40. The system 100 is configured to collect imaging data, such as, for example x-ray computed tomography (CT) or magnetic resonance imaging (MRI) data, from an object located within the bore of the gantry ring 40, in any manner known in the medical imaging field. As shown in FIGS. 1-3 and 5, the pedestal 50 is adapted to support a tabletop support 60 that can be attached to the pedestal 50 in a cantilevered manner and extend out into the bore of the gantry ring 40 to support a patient or other object being imaged. As shown in FIG. 4, the tabletop support 60 can be partially or entirely removed from the pedestal 50, and the gantry ring 40 can be rotated relative to the base 20, preferably at least about 90 degrees, from an imaging position (FIGS. 1-3 and 5) to a transport position (FIG. 4) to facilitate transport and/or storage of the imaging system.

Figure 5:
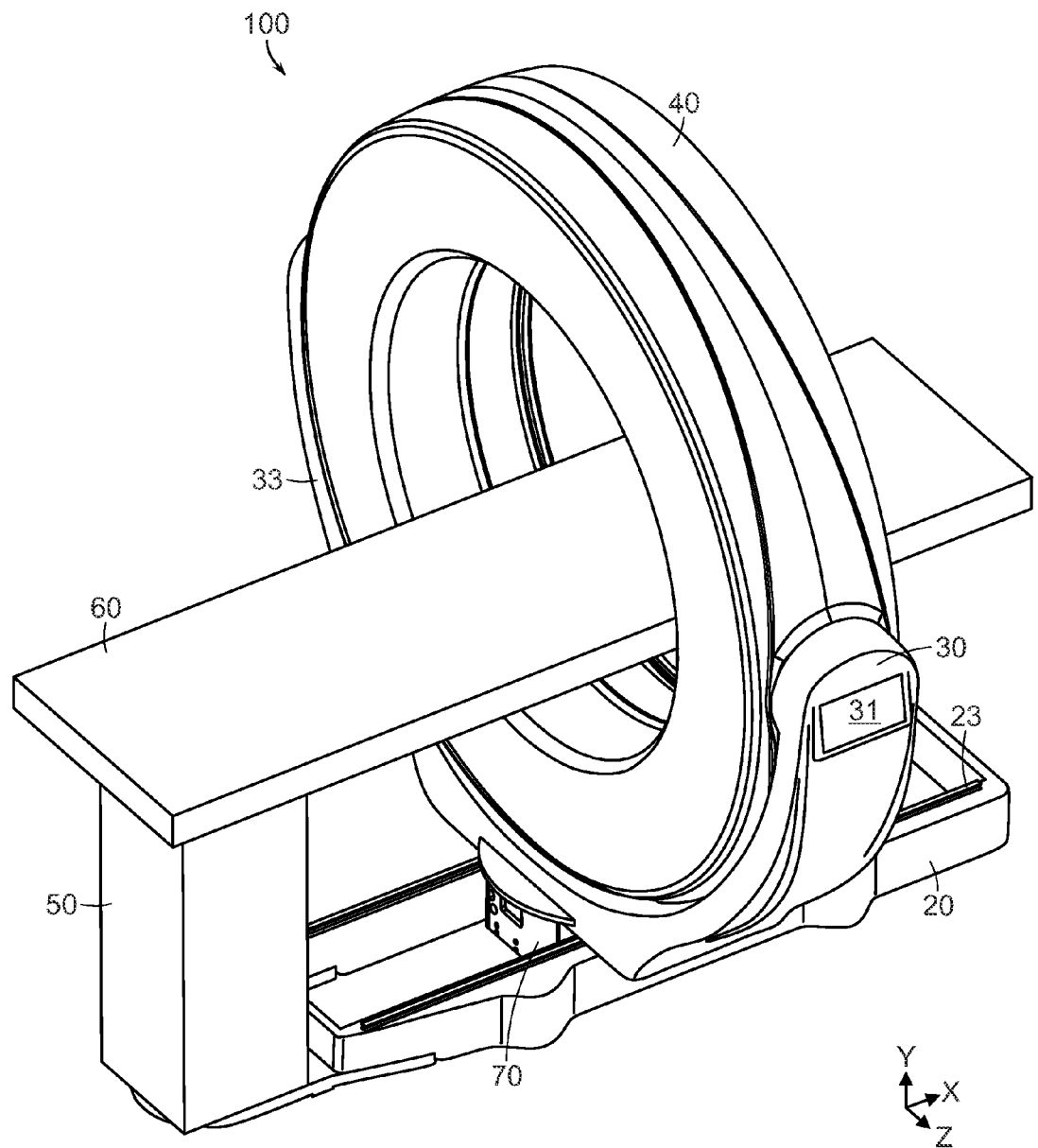
FIG. 5 is an isometric view of the mobile imaging system in a scan mode.
Figure 6:
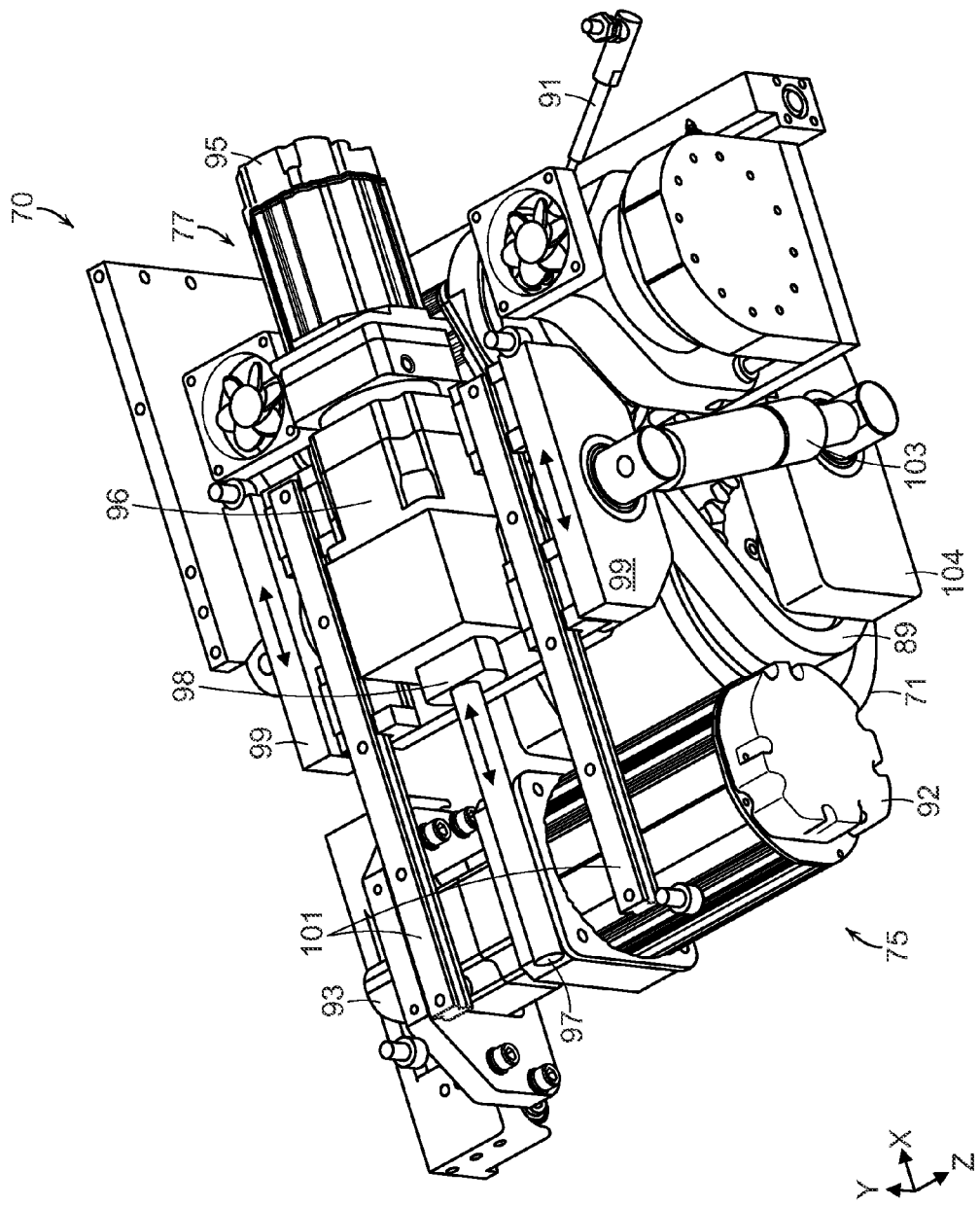
FIG. 6 is a top isometric view of the drive mechanism for an imaging system according to one embodiment.

As illustrated most clearly in FIGS. 3 and 5, the system 100 includes a drive mechanism 70. The drive mechanism 70 is mounted beneath the gimbal 30 and the gantry ring 40 and within the base 20. The drive mechanism 70 also comprises a drive wheel 71 that can extend and retract between a first extended position (FIG. 1) to facilitate transport of the imaging system 100, and a second retracted position (FIGS. 2 and 3) during an image acquisition procedure (e.g., scan). The drive mechanism 70 includes a main drive (described in further detail below) that is geared into the drive wheel 71 when the drive wheel 71 is in the first extended position (FIGS. 1 and 3) to propel the imaging system 100 across a floor or other surface, and thus facilitate transport and positioning of the system 100. According to one aspect, the drive wheel 71 is decoupled from the main drive when the drive wheel 71 is in the second retracted position (FIGS. 2 and 3), thus preventing the system 100 from back driving the main drive gearbox and motor during an imaging procedure.

Figure 1:
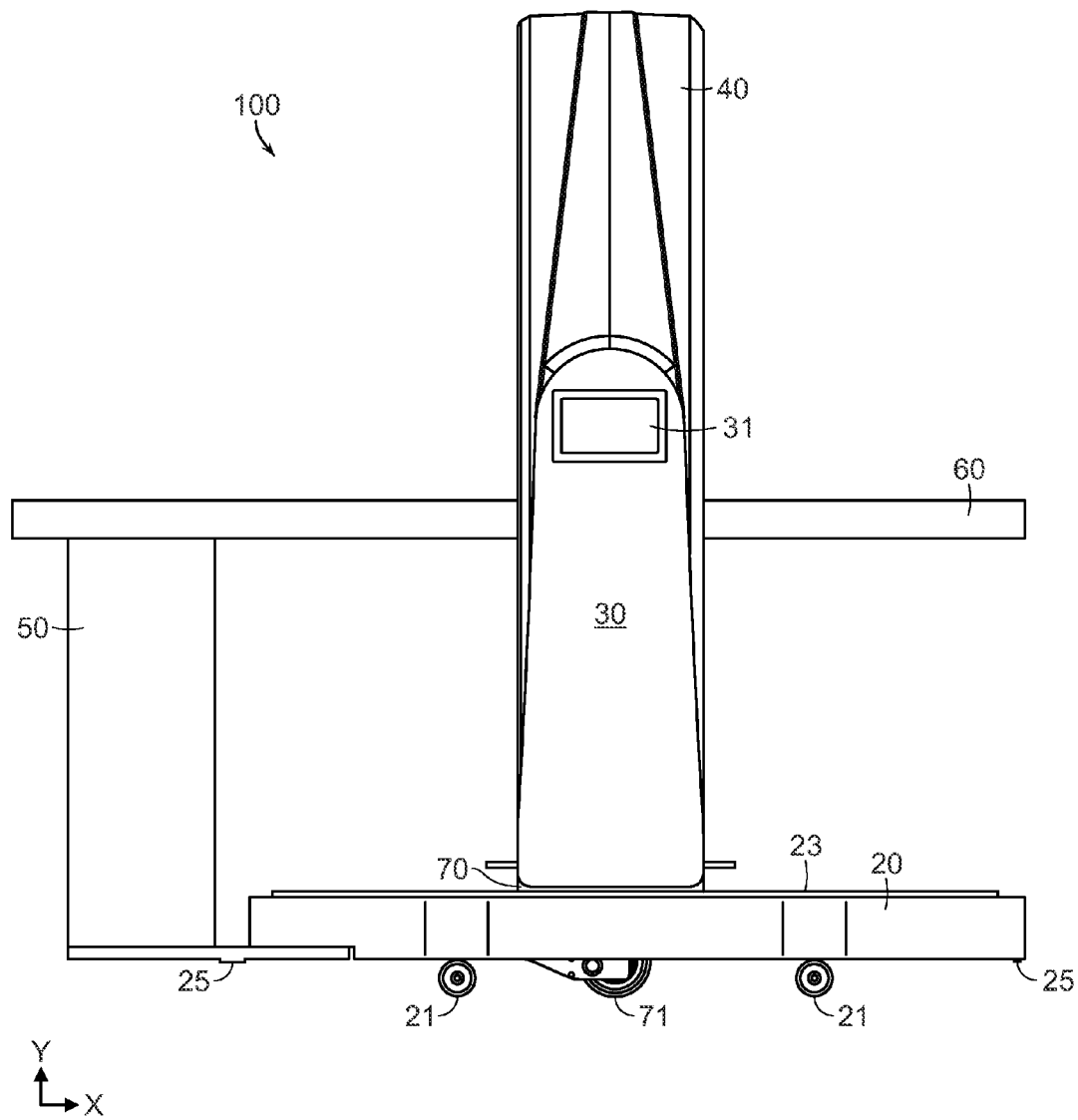
FIG. 1 is a side view of a mobile imaging system with a drive wheel and casters extended and the base of the system raised off the floor.

As is illustrated in FIGS. 3 and 5, the base 20 is a sturdy, generally rectilinear support structure. The base 20 includes a central opening extending lengthwise along the base, and the drive mechanism 70 is positioned inside the central opening. As seen in FIG. 3, the bottom of the base 20 includes a plurality of pockets that contain retractable casters 21. The casters 21 can be spring-loaded and biased to extend from the bottom of the base 20 when the system is raised off the ground, as shown in FIGS. 1 and 4. When the drive wheel 71 is retracted and the system 100 is lowered to the ground, as shown in FIG. 2, the casters 21 are retracted into their respective pockets. In an alternative embodiment, an active drive system, rather than a passive spring-based system, can drive the extension and retraction of the casters in their respective pockets.

The top of the base 20 is shown in FIG. 5, and includes a pair of parallel rails 23 running lengthwise on the top surface of the base, on either side of the central opening of the base. During an imaging scan, the gantry 40, gimbal 30 and drive mechanism 70 translate along an imaging axis relative to the base 20, pedestal 50 and patient support 60. Bearing surfaces, which can be located on or attached to the drive mechanism 50 and/or gimbal 30, mate with the rails 23 to guide the translation motion relative to the base. The drive mechanism 70 can include a scan drive (described in further detail below) that drives the translation motion of the drive mechanism 70, gimbal 30 and gantry 40 relative to the base 20.

The base 20 can be made compact and relatively lightweight to improve the portability and usability of the system 100. Minimizing the height and width of the base 20 minimizes interference with the operator's feet as the operator approaches a patient on the support table. A further advantage of this embodiment is that the wheels, including drive wheel 71 and casters 21, retract within the base during imaging, and thus cannot interfere with the operator. The drive mechanism 70 in this embodiment is small and compact, and is generally hidden beneath the gimbal 30 and gantry ring 40 and positioned inside the central opening of the base 20, and advantageously does not interfere with the operator or with the loading/unloading of a patient or patient support table. Positioning the wheels within the base also minimizes the risk of injury (e.g., running over a person's foot) during transport of the system. It will be further noted that in this embodiment, the width of the base 20 tapers at the end of the base supporting the pedestal 50. An advantage of this design is that it allows a cart or shuttle to more easily approach the pedestal-end of the system 100 in order to transfer a patient support table 60 to the top of the pedestal 50 for imaging, or to remove the support table 60 from the top of the pedestal 50 following imaging. The shape and size of the base 20 and pedestal 50 can be designed to mate with the cart to facilitate the interchange of patient support tables. Suitable patient support tables and transport carts are known in the art, and examples are described in the JUPITER system brochure (November/2008) from TRUMPF Medezin Systeme GmbH & Co. KG of Puchheim, Germany, the entire contents of which are incorporated herein by reference.

In one embodiment, the width of the base 20 is approximately equal to or less than the width of the patient support table. At its widest (e.g., from the outside of the caster pockets), the base 20 can be less than about 25 inches wide, and can be around 22 or 23 inches wide. The central opening of the base can be about 13 inches across, or any other suitable dimension to accommodate the drive mechanism 70. The base 20 is generally less than about 6 inches in height when the system is lowered on the floor. The drive mechanism 70 is preferably very compact to maximize the translation motion of the gantry ring 40 relative to the base 20 and the support table 60. In one embodiment, the gantry ring 40 can translate at least about 40 inches to 48 inches.

Conceptually, the imaging system 100 according to this embodiment can be considered to include two separate sub-assemblies. The first sub-assembly is comprised of the base 20, pedestal 50 and patient table 60. The second sub-assembly includes the drive mechanism 70, the gimbal 30 and the gantry ring 40. This second sub-assembly includes most or all of the imaging components on the gantry ring 40, and is generally much heavier than the first sub-assembly. By way of example, for an x-ray CT scanning system, the gimbal and gantry sub-assembly can weigh on the order of 1400 to 1500 lbs., whereas the base/pedestal/table sub-assembly typically only weighs about 1000 lbs. or less.

According to one aspect, the drive mechanism 70 supports the weights of the gimbal 30 and gantry ring 40 during imaging procedures as well as during transport of the system. The base 20 and pedestal 50 are supported on the casters 21 during transport of the system. During imaging, the base 20 is lowered and can be supported on the ground. The drive mechanism 70 is configured such that even when the drive wheel 71 is retracted (FIGS. 2 and 3), the wheel 71 still contacts the ground and supports the weight of the gantry and gimbal sub-assembly. The drive mechanism supports at least a portion of the weight of the gantry and gimbal sub-assembly—i.e. greater than 0% and up to 100% of the weight of these components. In one embodiment, at least 50% of the weight of gantry and gimbal is supported by drive mechanism 71. In other embodiments, at least 60%, at least 70%, at least 80%, at least 90% and more than 95% of the weight of the gimbal and gantry sub-assembly is supported by the drive mechanism 71.

With this arrangement, the comparatively heavier weight of the gimbal/gantry sub-assembly does not need to be supported by the base of the system, which means the base can be made smaller and lighter for improved portability. Further, since the imaging gantry is supported at all times at least in part by the drive mechanism, the gantry can translate a relatively long distance along the length of the base while minimizing the possibility of beam deflection, which can result in variations of the scan plane and negatively effect image reconstruction. As shown in FIG. 3, the bottom surface of the base 20 includes at least three pads 25 that define a single imaging plane. When the base 20 is lowered to the floor, the base 20 rests on the pads 25, which define a single reference plane for the base, pedestal and table assembly, which are fixed relative to the pads 25. The pads 25 maintain this reference plane even when there are elevation differences in the floor. The rails 23 of the base, upon which the gimbal and gantry translate, are similarly fixed in relation to the pads 25, and define an imaging plane, parallel to the reference plane, for the imaging components of the gantry. According to one aspect, the drive mechanism 70 includes a suspension system (described further below) between the drive wheel 71 and the gantry that supports the weight of the gimbal and gantry and allows the drive wheel to conform to elevation differences in the floor while the gimbal and gantry translate in the imaging plane defined by the rails, further minimizing deflection of the imaging plane path of the imaging components.

During transport mode, the drive mechanism 70 extends the drive wheel 71 downward as shown in FIGS. 1 and 4, which causes the base 20 to raise off the ground and the casters 21 to extend. As previously noted, the casters 21 can be spring-loaded to extend when the base 20 is lifted off the ground, or alternatively, they can be actively extended by a suitable drive apparatus. The drive mechanism 70 can include a suspension drive (described in further detail below) to drive the extension and retraction of the drive wheel 71. During transport mode, the drive mechanism 71, along with the gimbal 30 and gantry ring 40, can translate to the approximate center of the base 20, as shown in FIG. 4, so that these heavier components are approximately centered between the casters 21. This helps improve the balance and stability of the system during transport. The gimbal 30 and gantry ring 40 can be rotated into transport position, as shown in FIG. 4. A pin system can lock the drive mechanism 70, gimbal 30 and gantry ring 40 in place relative to the base 20 so that the entire system can be easily transported. The drive mechanism's main drive, which drives the drive wheel 71, can be servo-controlled, and the system 100 can be driven, in both forward and reverse directions, in response to a user input command. The suspension system of the drive mechanism 71 can be an active suspension system, as described below, which can aid in driving the imaging system 100 over uneven surfaces, such as thresholds and ramps. Steering of the system can be achieved by pivoting the system 100 around the centrally-located drive wheel 71, using the casters 21 for balance and support. A handle or other steering mechanism can be provided on the system (such as on the gimbal, gantry, or pedestal) to assist in driving the system. A strain gauge, throttle, button or other user-input mechanism located on the system can provide servo-feedback down to the drive mechanism to control the driving of the drive wheel 71. In one embodiment, shown in FIGS. 1-3 and 5, the system 100 can include a display system 31 that includes a camera on one side of the system and a display screen, such as an LCD display, on the opposite side of the system that allows the operator positioned behind the system to see obstacles in front of the system, which further assists the transport of the system. The system 100 can include a collision detection system, such as an audio or visual range-finder device, to further assist in transporting the device.

Turning now to FIGS. 6-16, a drive mechanism 70 in accordance with one embodiment of the invention is shown. The drive mechanism 70 can include three drive systems: a main drive assembly 73 that is coupled to and drives the drive wheel 71 for transporting the imaging system, a scan drive assembly 75 for translating the imaging components relative to the system base during an imaging scan, and a suspension drive assembly 77 that controls the extension and retraction of the drive wheel 71.

The main drive 73 is shown most clearly in FIGS. 7, 11A, 11B, and 16, and includes a motor 81, a sprocket 83 that can be connected by a drive chain 89 (FIG. 6) to the drive wheel 71, a gearbox 82, a sliding yoke 84, and a brake mechanism 86. As noted above, the main drive 73 is engaged to the drive wheel 71 when the wheel is extended in transport mode, and is de-coupled from the drive wheel when the wheel is retracted during an imaging mode. The engagement and disengagement of the drive wheel 71 is accomplished by the sliding yoke 84, which is connected to a main drive decoupling linkage 91 (FIGS. 12B and 13). As the drive wheel 71 retracts and extends, the decoupling linkage 91, which can be a rotating piston and sleeve assembly, causes the yoke 84 to reciprocate, as shown by the arrow in FIG. 7. This causes a sliding spline 85 (FIG. 16), connected to the yoke 84, to move in and out of mating engagement with the sprocket 83, thereby controlling the engagement and disengagement of the drive wheel 71 from the motor 81 and gearbox 82. The yoke 84 and spline 85 can be spring-biased into a disengaged position, and only when the drive wheel is in an extended position does the wheel 71 become engaged to the main drive.

Figure 7:
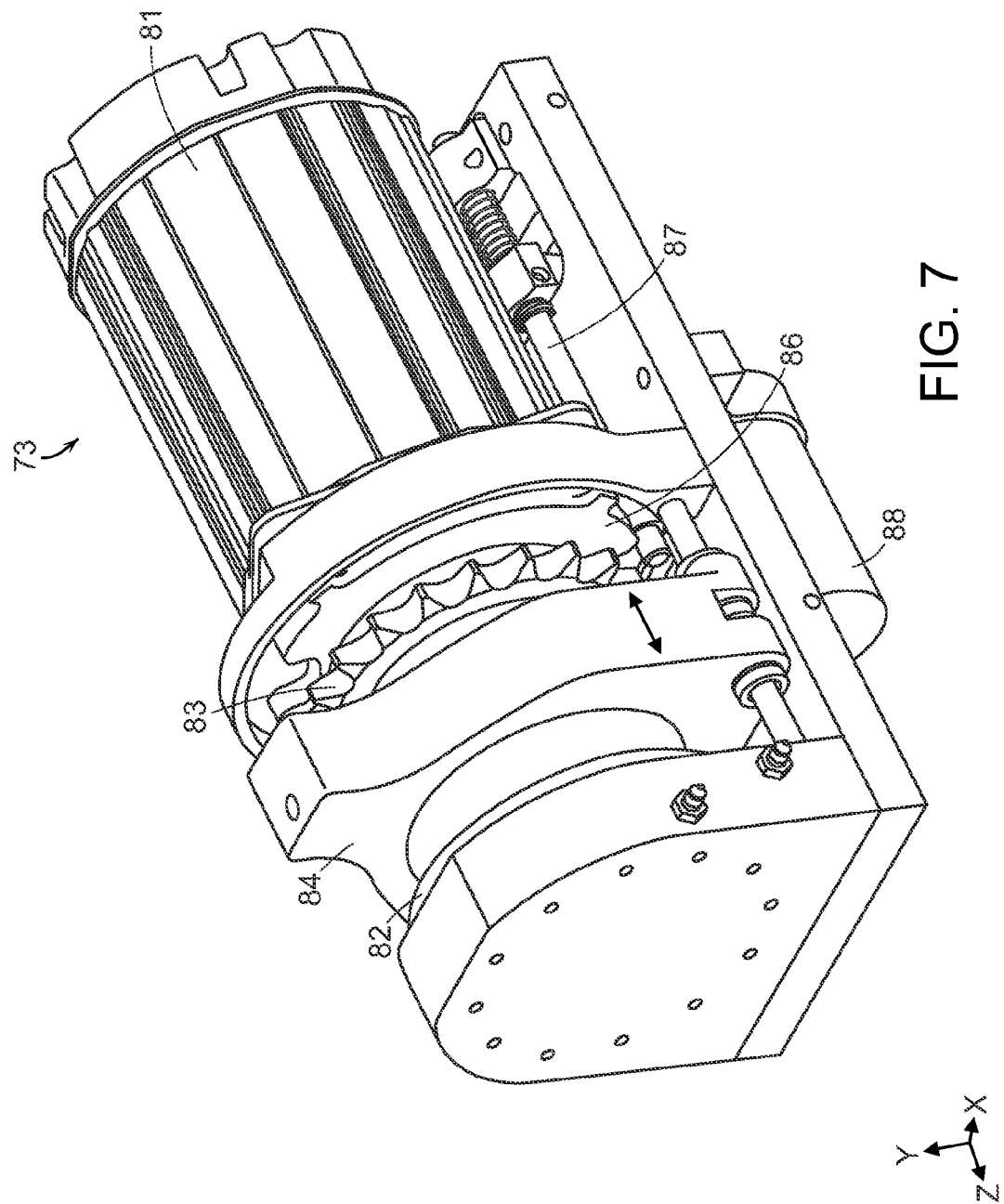
FIG. 7 is an isometric view of the main drive assembly.

The main drive 73 also includes a brake mechanism, which includes a rotating brake disc 86, a spring-loaded brake rod 87, and a brake solenoid 88. The brake disc 86 can be coupled to the sprocket 83. The brake rod 87 can be biased to extend beyond the brake disc 86, as shown in FIG. 7, which prevents the sprocket 83 and drive wheel 71 from rotating. The brake mechanism thus functions similar to a parking brake in an automobile. When the solenoid 88 is energized, it drives the brake rod 87 to retract away from the brake disc 86, which is then free to rotate along with the sprocket 83 and drive wheel 71. An important safety feature of this design is that if the imaging system 100 loses power, the brake rod automatically extends to stop the motion of the drive wheel 71.

Figure 8:
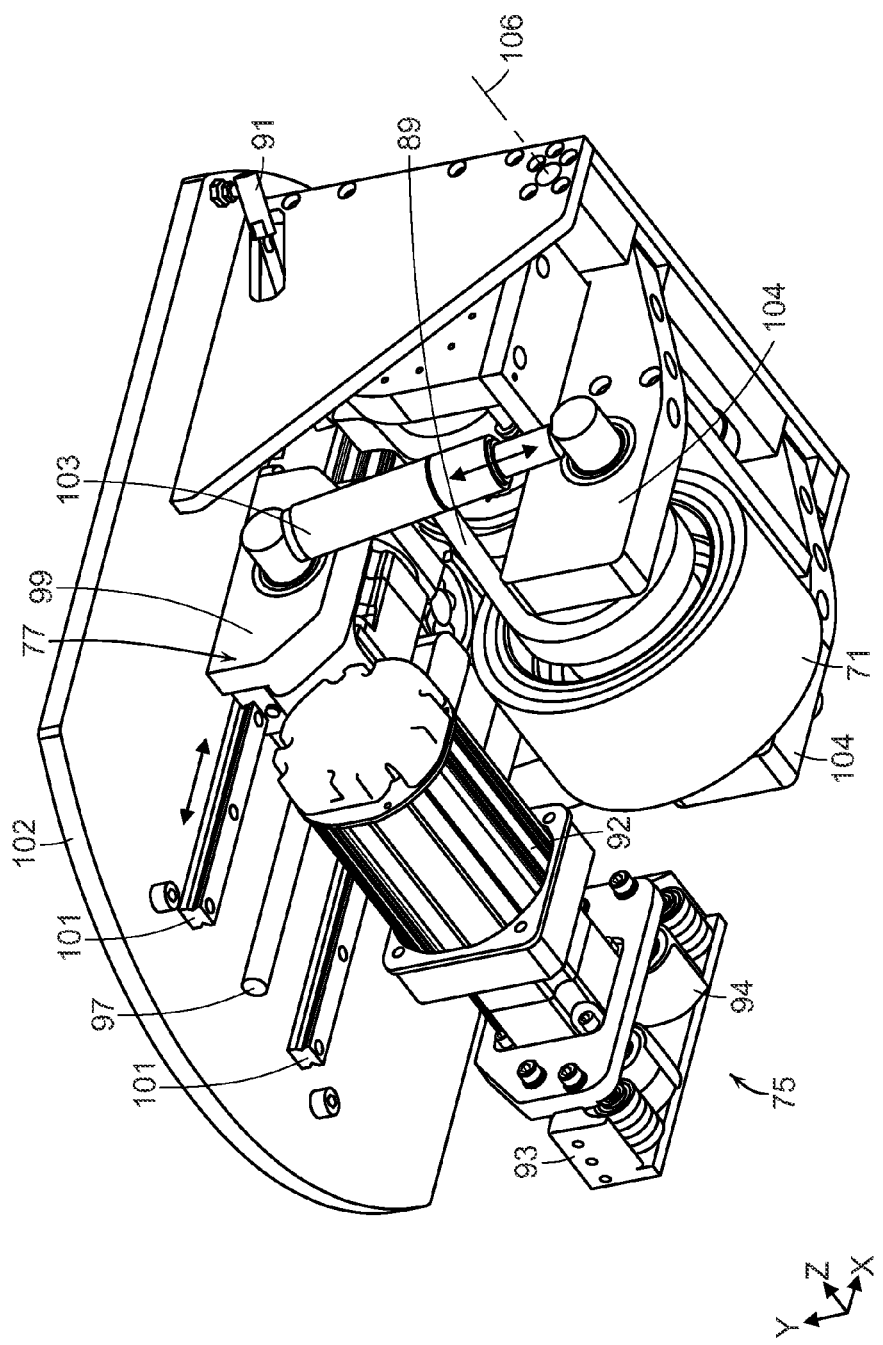
FIG. 8 is a bottom isometric view of the drive mechanism.
Figure 9:
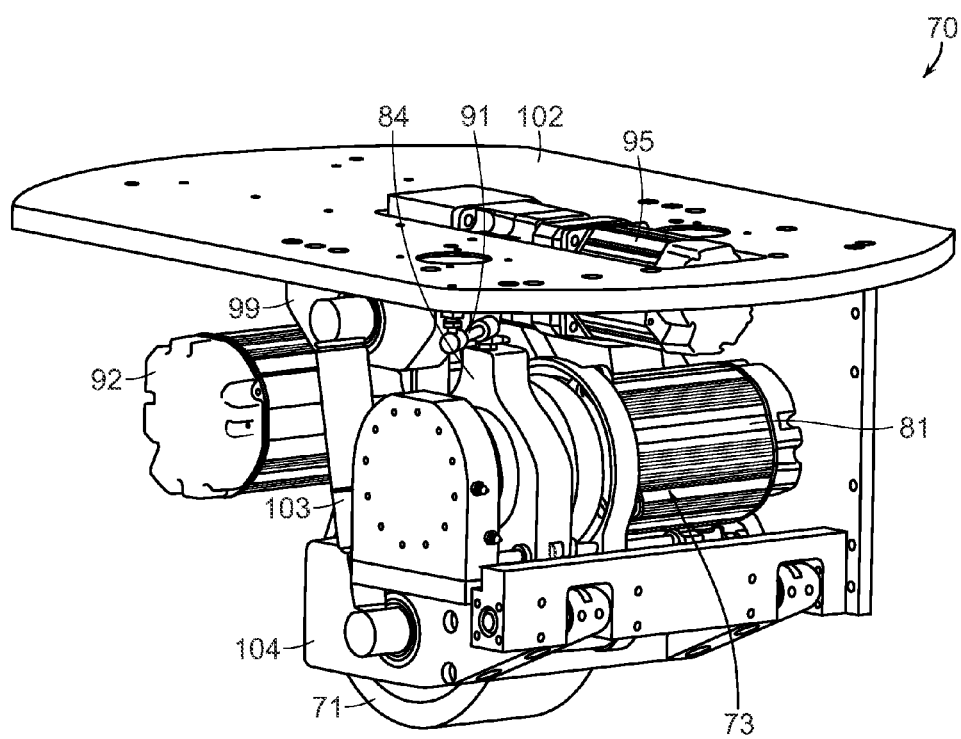
FIG. 9 is a rear isometric view of the drive mechanism.
Figure 10:
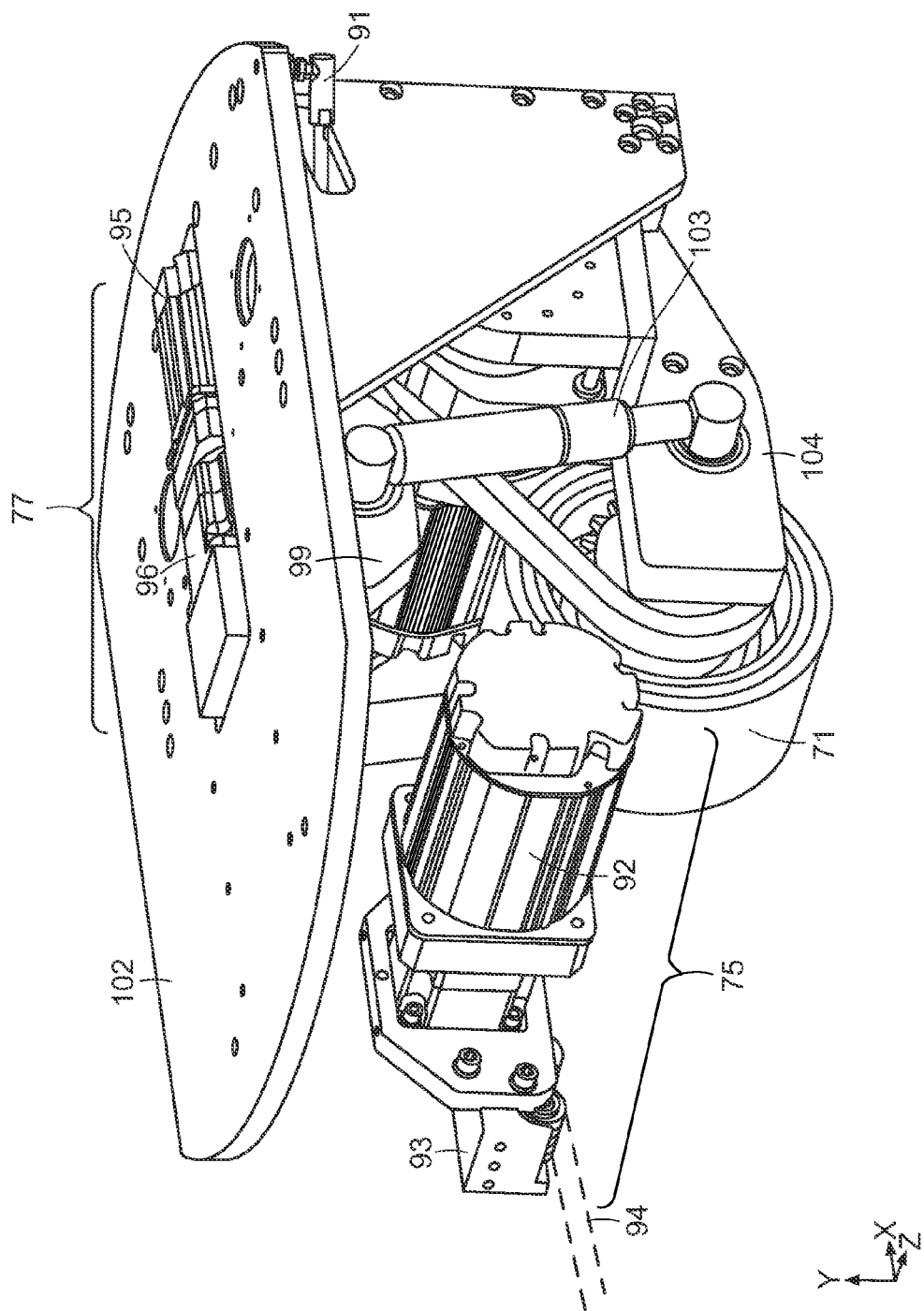
FIG. 10 is a front isometric view of the drive mechanism.
Figure 11A:
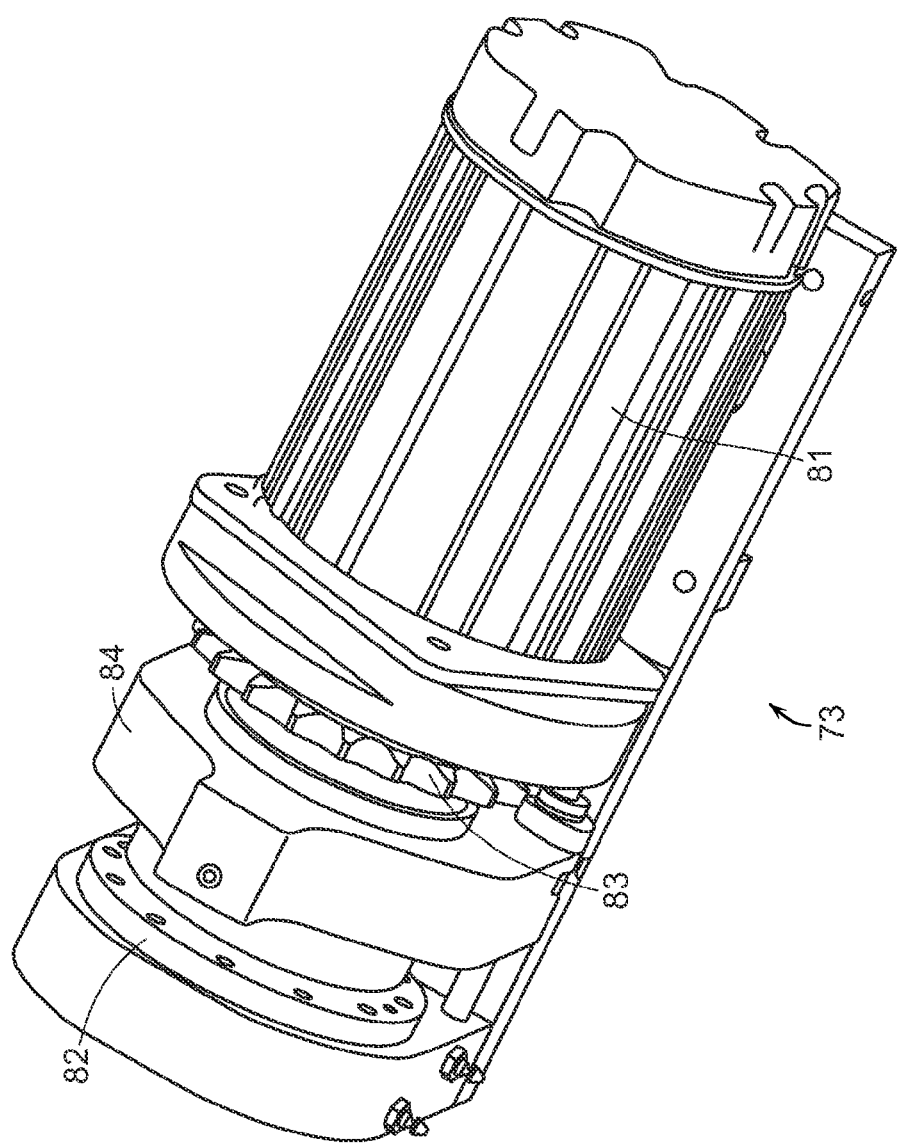

The scan drive assembly 75 is shown in FIGS. 6, 8-10 and 12A-13. The scan drive assembly 75 drives the translation of the drive mechanism 70, gimbal 30 and gantry ring 40 relative to the base 20. In this embodiment, the scan drive assembly 75 is mounted adjacent the main drive assembly 73 and drive wheel 71. All of these components are mounted beneath the gimbal 30 and gantry ring 40 in a compact space, generally in the opening within the base 20. The scan drive assembly 75 in this embodiment includes a motor 92 and a belt drive 93, which is shown most clearly in FIGS. 8 and 10. The belt drive 93 mates with a bearing surface on the base 20 in order to effect the translation of the drive mechanism, gimbal and gantry ring relative to the base. In one embodiment, the belt drive 93 mates with a bearing surface, which can be a lip or rail (not shown), provided on an interior wall of the central opening of the base 20 (FIGS. 3 and 5). A belt 94 is secured to the bearing surface and is looped through the belt drive 93, where it meshes with a pulley driven by the scan drive motor 92, as shown in FIGS. 8 and 10. The rotation of the scan drive motor 92 thus causes the scan drive assembly 75 to traverse along the length of the belt 94, and thereby translate the gantry, gimbal and drive mechanism relative to the base. The belt drive 93 can be servo-controlled, with a linear encoder device, and have substantially zero or minimal backlash, to provide precise, controlled fine-scanning of the imaging components relative to the base and patient support table. Any suitable configuration for achieving translation using a scan drive disposed within the drive mechanism can be employed.

The suspension drive assembly 77 is shown most clearly in FIGS. 6, 8-10, and 12A-15. The suspension drive assembly comprises a motor 95 and gearbox 96 that drive the rotation of a lead screw 97. A lead screw nut 98 translates with the rotation of the lead screw 97, as indicated by the "nut travel" arrow shown in FIG. 6. The lead screw nut 98 is mechanically coupled to a pair of rail carriages 99, so that the translation of the lead screw nut 98 causes the rail carriages 99 to translate on a pair of rails 101 that are fixed to the upper plate 102 of the drive mechanism 70, as shown in FIG. 8. The rail carriages 99 are each connected to one end of a spring 103, which can be a gas spring, as shown in FIG. 8. The other end of each spring 103 is connected a respective swing arm 104 that can pivot with respect to the drive mechanism around an pivot axis 106. As can be seen in FIG. 8, for example, the translation of the rail carriages 99 causes the springs 103 to articulate with respect to the rail carriages 99 and the swing arms 104, which in turn causes the swing arms 104 to pivot, as shown generally by the arrow in FIG. 8. The drive wheel 71 is mounted between the two pivoting swing arms 104, so that the translation of the rail carriages 99 and the resulting pivoting motion of the swing arms 104 causes the drive wheel 71 to extend and retract relative to the upper plate 102 of the drive mechanism 70.

Figure 12A:
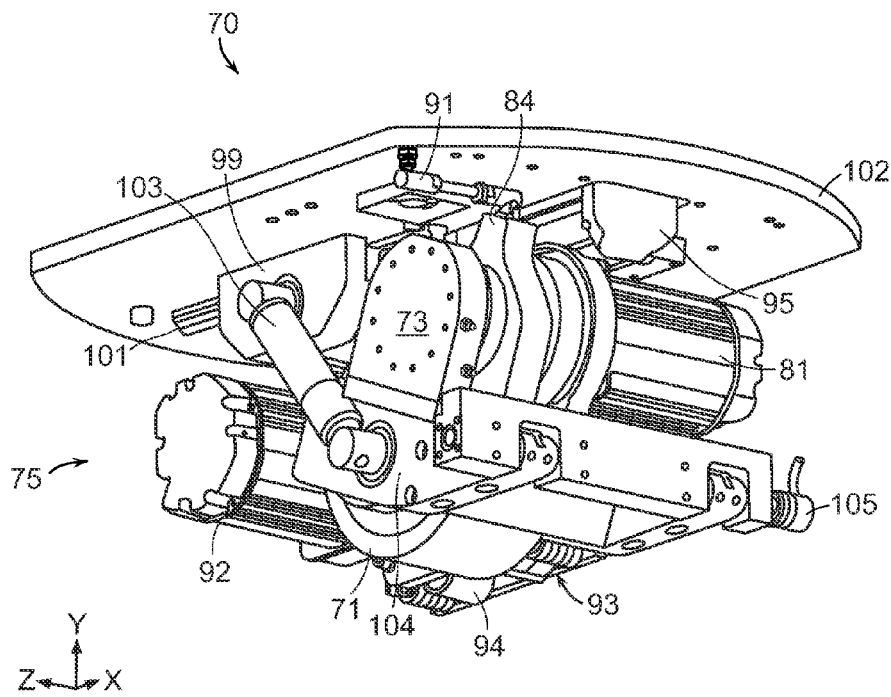
FIGS. 12A and 12B are bottom isometric views of the drive mechanism.
Figure 12B:
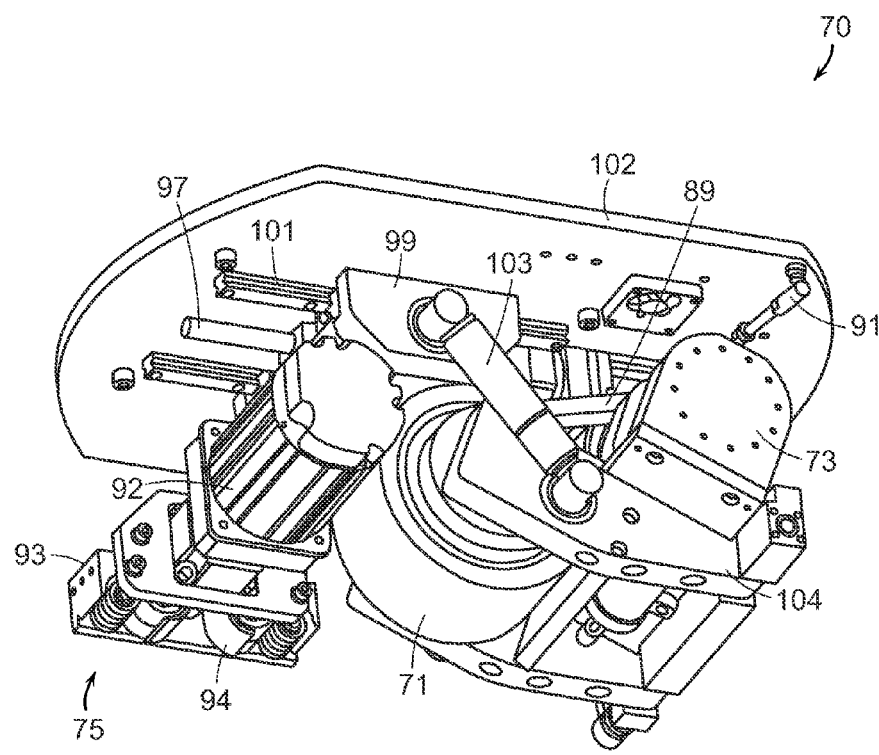
Figure 13:
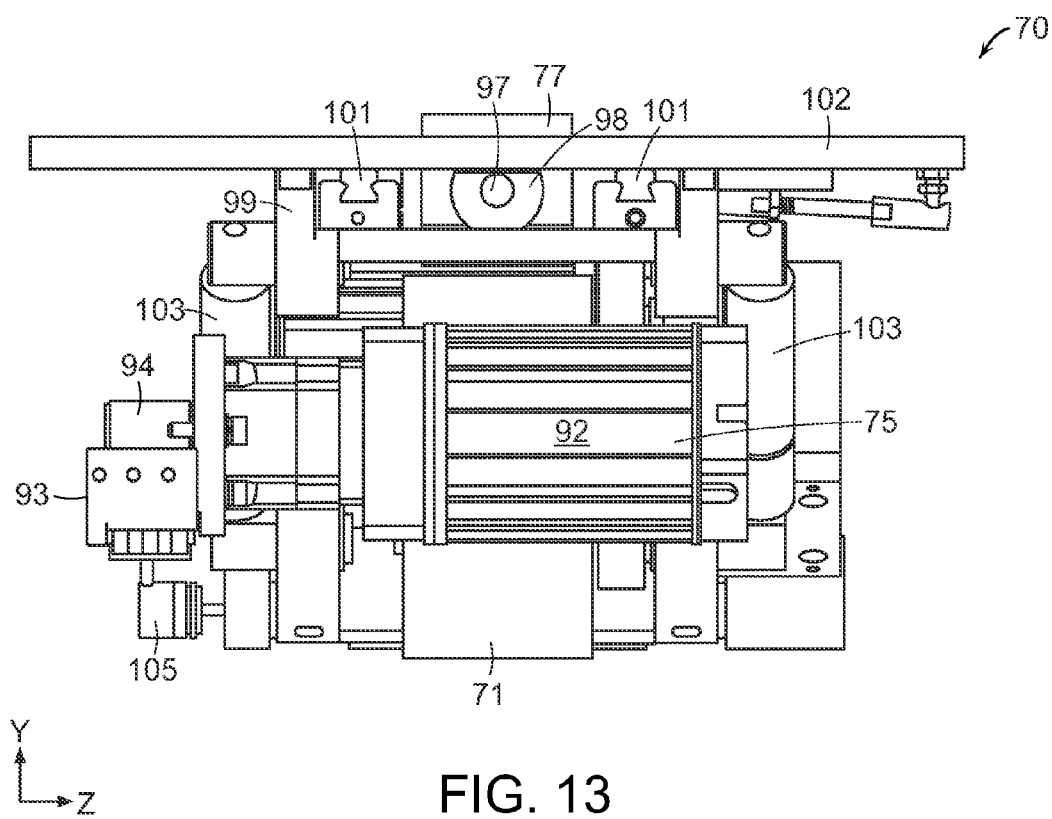
FIG. 13 is a front view of the drive mechanism.
Figure 14:
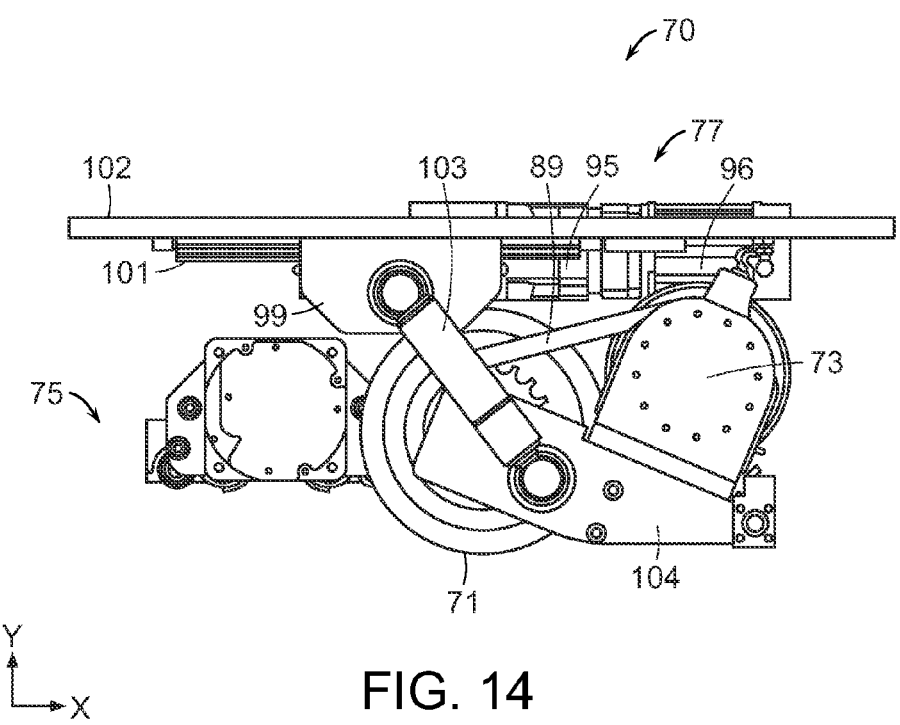
FIG. 14 is a side view of the drive mechanism.
Figure 15:
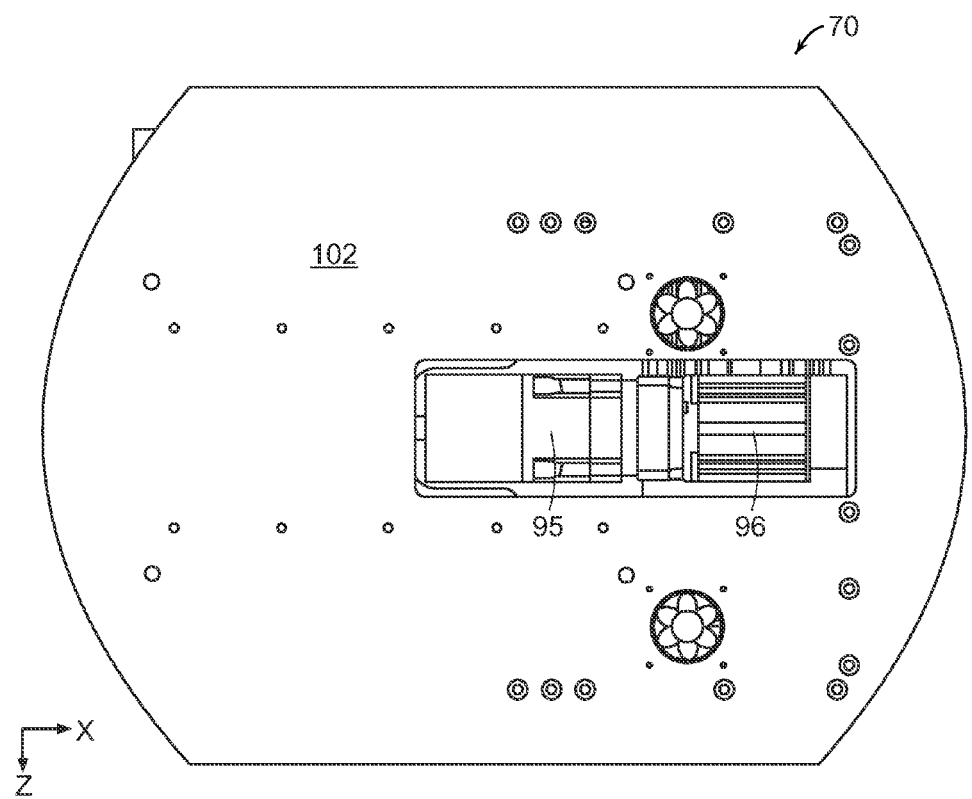
FIG. 15 is a top view of the drive mechanism.
Figure 16:
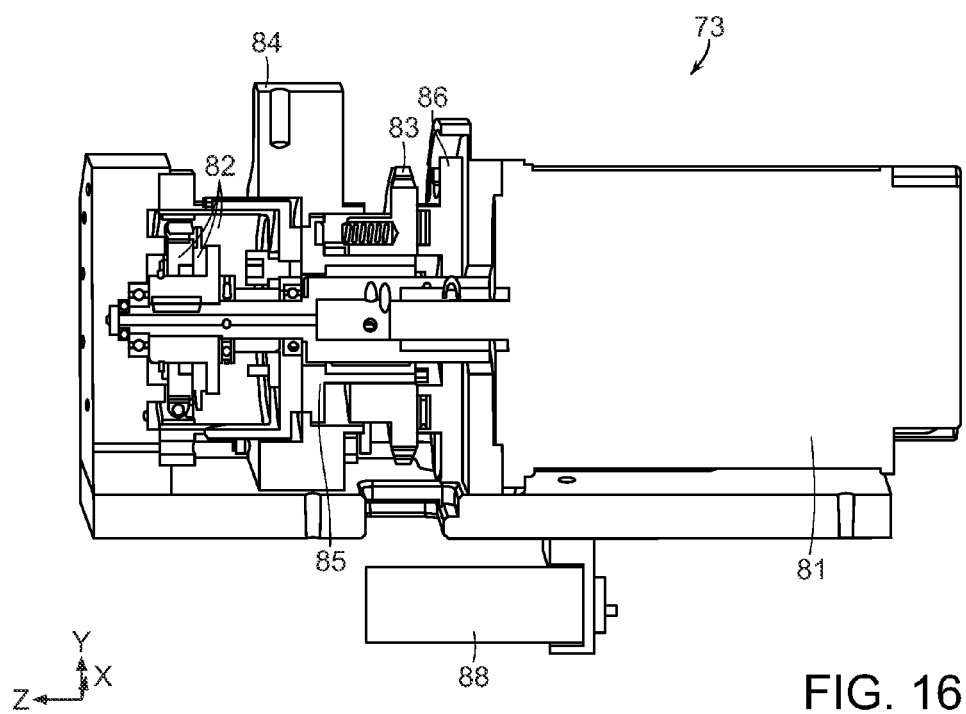
FIG. 16 is a cross-sectional view of the main drive assembly.

As can be seen in FIGS. 12A and 12B, the main drive 73 can be mounted to the swing arms 104. In this way, as the rail carriages 99 translate causing the swing arms 104 to pivot, the main drive engagement/disengagement linkage 91, which connects the upper plate 102 of the drive mechanism 71 to the sliding yoke 84 of the main drive 73, acts on the sliding yoke 84 to selectively engage and disengage the main drive 73 to and from the drive wheel 71. As previously discussed, in one embodiment, the drive wheel 71 is engaged to the main drive 73 only when it is in an extended position—i.e., when the swing arms 104, main drive 73 and drive wheel 71 are pivoted down and away from the upper plate 102 of the drive mechanism 70. When the drive wheel 71 is retracted—i.e., the swing arms 104, main drive 73 and drive wheel 71 are pivoted upwards towards the upper plate 102, the yoke 84 slides back to disengage the main drive 73 from the drive wheel 71.

It will be noted that when the drive wheel 71 is retracted, the base 20 automatically lowers to the ground and rests on pads 25, as shown in FIGS. 2, 3 and 5. During an imaging scan, the weight of the gimbal 40 and gantry 30 remains supported by the drive wheel 71, which is able to freely-rotate as the gimbal and gantry translate on the rails 23 of the base. One advantage of this configuration is that the heavy gimbal and gantry ring assembly can be easily moved manually relative to the base, such as may be required in order to quickly access a patient during an emergency situation.

The springs 103 function as a suspension system between the drive wheel 71 and the gimbal 30 and gantry ring 40, which are supported by the drive wheel 71 during both transport and imaging modes. The springs 103 can contract to allow the wheel 71 to conform to elevation differences in the floor during an imaging scan, while the drive mechanism 70, gimbal 30 and gantry ring 40 translate on the base 20 during an imaging scan. This can greatly reduce or eliminate deflection of the scan plane path of the imaging components during the fine movement scan. During transport of the system 100, the springs 103 can facilitate transport of the system over uneven surfaces, including door thresholds and ramps, for example. In one embodiment, the suspension system is an active suspension system that can maintain a controlled force between the drive wheel and the floor. In this embodiment, the springs 103 and suspension drive assembly 77 can include an active servo-control system that can continually adjust the translation of the rail carriages to maintain a substantially constant spring displacement, and thus maintain a substantially constant force between the wheel and the floor. As shown in FIGS. 12A and 13, for example, an encoder 105 can be provided on at least one of the swing arms 104 to measure the displacement of the swing arm 104 and spring(s) 103 relative to the upper plate 102. The encoder 105 can provide a feedback signal to the suspension drive 77 to make continual fine adjustments and control the force between the wheel and the floor.

The drive wheel 71 can comprise a suitable elastomeric material that is rated to safely support the weight of the imaging components in the gimbal and gantry ring assembly. For example, the wheel can be rated to support about 1900 lbs. A softer durometer material for the wheel will provide better grip and minimize the risk of slippage, but may not be rated to support the required weights.

An advantage of the present drive mechanism 71 is that it is easily accessible for servicing and repair. For example, the drive wheel can be extended to raise the system off the floor and provide easy access to any components of the drive mechanism 71. If the drive mechanism 71 needs to be removed, the system can be put on blocks, and the entire drive mechanism can be taken out at once, such as by removing the upper plate of the drive mechanism from the bottom of the gimbal 30.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A drive mechanism for a mobile imaging system, comprising:
   a drive wheel;
   a main drive mechanically coupled to the drive wheel for propelling the imaging system, including a base and one or more imaging components, across a surface in a transport mode; and
   a translation mechanism that translates the one or more imaging components along an axis relative to the base in an imaging mode, the drive wheel supporting the one or more imaging components at least in part in both the transport mode and the imaging mode, wherein the drive mechanism is mounted to the imaging components and supports the weight of the imaging components but not the base during transport of the system.

2. The drive mechanism of claim 1, wherein the translation mechanism comprises a scan drive that translates the one or more imaging components along an axis relative to the base to provide an imaging scan.

3. The drive mechanism of claim 2, wherein the drive mechanism can be decoupled from the drive wheel to allow the imaging components to be driven by the scan drive for fine scanning movements while the drive wheel continues to support the load of the imaging components.

4. The drive mechanism of claim 1, further comprising: a suspension drive that extends the drive wheel relative to a bottom surface of the base when the imaging system is in a transport mode and retracts the drive wheel relative to the bottom surface of the base when the imaging system is in an imaging mode.

5. The drive mechanism of claim 4, further comprising: an active suspension system that is controlled by the suspension drive.

6. The drive mechanism of claim 4, wherein the main drive, the scan drive and the suspension drive are compactly mounted beneath the imaging components to allow maximum travel of the imaging components along the length of the base.

7. The drive mechanism of claim 1, wherein the drive wheel retracts for lowering the base onto the floor during an imaging mode and extends for raising the base from the floor during a transport mode.

8. The drive mechanism of claim 1, wherein the weight of the imaging components is supported by the drive mechanism during both transport and imaging modes.

9. The drive mechanism of claim 1, further comprising a plurality of casters attached to the base, and the casters are extended and retracted relative to a bottom surface of the base to raise and lower the base and a table system mounted to the base in coordination with an extension and retraction of the drive wheel relative to the main drive.

10. The drive mechanism of claim 9, wherein the drive mechanism is generally centrally located between the plurality of casters in the transport mode to balance the system in the transport mode.

11. The drive mechanism of claim 10, wherein steering is achieved by pivoting the system around the drive mechanism.

12. The drive mechanism of claim 9, wherein the drive wheel and casters are located beneath the base and do not interfere with a user approaching the base of a table system mounted to the base.

13. The drive mechanism of claim 12, wherein the base is less than about 25 inches in width and less than about 6 inches in height when the base rests on the floor.

14. The drive mechanism of claim 13, wherein the base is configured to allow a can to approach the base for mounting a table onto the base without interference from the drive mechanism or casters.

15. The drive mechanism of claim 1, further comprising a rail system that couples the imaging components to the base, the imaging components translating relative to the base on the rail system during an imaging scan.

16. The drive mechanism of claim 1, further comprising a suspension system that reduces or eliminates deflection of a scan plane path of the imaging components during the imaging scan.

17. The drive mechanism of claim 1, wherein the drive mechanism is mounted at least partially inside and beneath the base.

18. The drive mechanism of claim 1, wherein the drive mechanism can be decoupled from the drive wheel to allow the imaging components to moved manually relative to the base.

19. The drive mechanism of claim 1, wherein the drive mechanism can be decoupled from the drive wheel to allow the entire imaging system to be moved manually.

20. The drive mechanism of claim 1, further comprising a brake system to stop all motion of the imaging components relative to the floor.

21. The drive mechanism of claim 1, wherein the drive mechanism raises off the floor allowing removal of all or a portion of the drive mechanism from the imaging system for service and repair purposes.

22. The drive mechanism of claim 1, wherein the imaging components are housed in a gantry ring that is supported above the drive mechanism.

23. The drive mechanism of claim 1, further comprising a servo-control system, coupled to the main drive, that causes the main drive to propel the imaging system in a transport mode in response to a user input command.

24. The drive mechanism of claim 23, further comprising a user input mechanism that provides commands to the servo-control system.

25. The drive mechanism of claim 24, wherein the user input mechanism comprises one or more of a handle, a steering mechanism, a throttle, a button and a strain-gauge.

26. A drive mechanism for a mobile imaging system, comprising:
a drive wheel;
a main drive mechanically coupled to the drive wheel for propelling the imaging system, including a base and one or more imaging components, across a surface in a transport mode;
a translation mechanism that translates the one or more imaging components along an axis relative to the base in an imaging mode, the drive wheel supporting the one or more imaging components at least in part in both the transport mode and the imaging mode; and
a plurality of casters attached to the base, and the casters are extended and retracted relative to a bottom surface of the base to raise and lower the base and a table system mounted to the base in coordination with an extension and retraction of the drive wheel relative to the main drive, wherein the weight of the base and the table system are supported by the casters in transport mode.

27. A drive mechanism for a mobile imaging system, comprising:
a drive wheel;
a main drive mechanically coupled to the drive wheel for propelling the imaging system, including a base and one or more imaging components, across a surface in a transport mode;
a translation mechanism that translates the one or more imaging components along an axis relative to the base in an imaging mode, the drive wheel supporting the one or more imaging components at least in part in both the transport mode and the imaging mode;
a plurality of casters attached to the base, and the casters are extended and retracted relative to a bottom surface of the base to raise and lower the base and a table system mounted to the base in coordination with an extension and retraction of the drive wheel relative to the main drive; and
at least three pads that are attached to bottom of the base and sit on the floor when the base is lowered to define a scan plane, wherein the weight of the base and table are supported by the pads and/or casters during the imaging mode.

28. A drive mechanism for a mobile imaging system, comprising:
- a drive wheel;
- a main drive mechanically coupled to the drive wheel for propelling the imaging system, including a base and one or more imaging components, across a surface in a transport mode;
- a translation mechanism that translates the one or more components along an axis relative to the base in an imaging mode, the drive wheel supporting the one or more imaging components at least in part in both the transport mode and the imaging mode; and
- a suspension system that reduces or eliminates deflection of a scan plane path of the imaging components during the imaging scan, wherein the suspension system allows the drive wheel to conform to elevation differences in the floor while a rail system on the base maintains the plane of the imaging components.

29. The drive mechanism of claim 28, wherein the suspension system maintains a controlled force between the drive wheel and the floor.

30. The drive mechanism of claim 28, wherein the suspension system comprises an active suspension system.

31. The drive mechanism of claim 28, wherein the suspension system enables the system to be transported over uneven surfaces.

32. A mobile imaging; system, comprising:
- a base;
- a gantry having one or more imaging components;
- a drive wheel that supports the gantry; and
- a drive mechanism that includes a main drive coupled to the drive wheel for transporting the base and gantry and a translation mechanism that translates the gantry and drive wheel relative to the base during an imaging scan.

33. The mobile imaging system of claim 32, further comprising a gimbal that supports the gantry, the gimbal being supported by the drive wheel.

34. The mobile imaging system of claim 32, wherein the base includes a central opening and the drive wheel is located within the central opening.

35. The mobile imaging system of claim 32, further comprising a patient table supported by the base.

36. The mobile imaging system of claim 32, wherein the drive mechanism includes a suspension drive that extends and retracts the drive wheel relative to the drive mechanism.

37. The mobile imaging system of claim 36, wherein extending the drive wheel causes the base to rise off the around and retracting the drive wheel causes the base to lower to the ground.

38. The mobile imaging system of claim 37, wherein the base includes at least three support pads on a bottom surface of the base that define an imaging reference plane when the base is lowered to the ground.

39. The mobile imaging system of claim 38, wherein the base further comprises a rail system that defines an imaging plane, parallel to the reference plane, the translation mechanism translating the gantry on the rail system.

40. The mobile imaging system of claim 32, wherein the imaging system is an x-ray computed tomography (CT) system.

41. The mobile imaging system of claim 32, wherein the imaging system is a magnetic resonance imaging system.

42. A method of imaging a patient, comprising:
- transporting an imaging system, including a base, a drive mechanism and one or more imaging components, by driving a drive wheel mechanically coupled to the drive mechanism;
- retracting the drive wheel relative to the drive mechanism to lower the base to the ground;
- positioning a patient on a patient support mounted to the base; and
- translating the imaging components relative to the base and the patient to obtain imaging data from the patient, while the imaging components are supported by the drive wheel.

43. The method of claim 42, further comprising:
- extending the drive wheel relative to the drive mechanism to raise the base from the ground; and
- transporting the imaging system.

* * * * *